United States Patent [19]

O'Neill et al.

[11] Patent Number: 5,097,072
[45] Date of Patent: Mar. 17, 1992

[54] PREPARATION OF POLYAMINES

[75] Inventors: Gerald J. O'Neill, Arlington, Mass.; Albert H. Levesque, Nashua, N.H.

[73] Assignee: W.R. Grace & Co.-Conn., New York, N.Y.

[21] Appl. No.: 674,860

[22] Filed: Mar. 21, 1991

Related U.S. Application Data

[63] Continuation-in-part of Ser. No. 475,557, Feb. 5, 1990, abandoned, which is a continuation-in-part of Ser. No. 306,930, Feb. 7, 1989, abandoned.

[51] Int. Cl.$^5$ .............................................. C07C 45/44
[52] U.S. Cl. .................................... 564/491; 564/492
[58] Field of Search ........................ 564/490, 491, 492

[56] References Cited

U.S. PATENT DOCUMENTS

| | | | |
|---|---|---|---|
| 3,565,957 | 1/1971 | Mirviss et al. | 564/491 |
| 3,700,598 | 10/1972 | Plonsker et al. | 262/50 |
| 4,235,821 | 6/1980 | Butte, Jr. et al. | 564/491 |
| 4,375,003 | 12/1983 | Allain et al. | 564/492 |
| 4,491,673 | 7/1985 | Cutchens et al. | 564/492 |
| 4,721,811 | 3/1988 | Sherwin et al. | 564/491 |
| 4,885,391 | 12/1989 | Herkes | 564/491 |
| 4,906,783 | 3/1990 | Smiley | 564/492 |

FOREIGN PATENT DOCUMENTS

| | | | |
|---|---|---|---|
| 140775 | 9/1948 | Australia | 564/492 |
| 544655 | 8/1957 | Canada . | |
| 201848 | 9/1987 | Japan | 564/491 |
| 711654 | 7/1954 | United Kingdom . | |
| 143390 | 2/1969 | United Kingdom | 564/492 |

*Primary Examiner*—Glennon H. Hollrah
*Assistant Examiner*—Scott C. Rand
*Attorney, Agent, or Firm*—Beverly K. Johnson

[57] ABSTRACT

Polyamines are prepared via the batchwise hydrogenation of polynitriles by the gradual addition of the polynitrile into a fed-batch reactor which contains chromium promoted Raney® cobalt catalyst. The hydrogenation optionally is conducted in the presence of anhydrous ammonia. The polyamine product having amino groups which corresponds to the nitrile of the polynitrile is economically obtained in high selectivity and yield as the dominant product.

14 Claims, No Drawings

PREPARATION OF POLYAMINES

This application is a continuation-in-part application of U.S. application having Ser. No. 475,557, filed Feb. 5, 1990 which is a continuation-in-part application of U.S. application having Ser. No. 306,930, filed Feb. 7, 1989, now abandoned.

BACKGROUND OF THE INVENTION

The present invention relates to an improved process for forming non-cyclic, aliphatic compounds having a multiplicity of primary amino groups and forming these compounds in high yields and selectivity from the corresponding polynitrile having at least 2 atoms between the cyano groups.

The hydrogenation of a wide variety of nitriles to their corresponding amines using conventional hydrogenation catalysts is well known. However, it is recognized that this mode of synthesis leaves much to be desired when the aim is to produce non-cyclic, aliphatic polyamines from polynitriles having an atomic structure capable of forming ring containing compounds. The presently known processes often provide the desired noncyclic products in low selectivity and yield, while the undesired cyclic compounds predominate. This is especially true with polynitriles such as nitrilotriacetonitrile (NTAN), iminoodiacetonitrile (IDAN) and ethylenediaminetetraacetonitrile (EDTN). Normally, the dominant products formed are cyclic polyamines. When one attempts to adjust the reaction conditions to those which may provide higher selectivity or yield of the noncyclic, aliphatic compound, one observes rapid inactivation of the catalyst materials used.

It is generally known that hydrogenation of nitriles can be accomplished by many modes such as by batch processing using a stirred autoclave or by continuous processing using a fixed bed reactor to contact a hydrogenation catalyst with a solution containing a nitrile. The reaction product is generally a mixture of primary, secondary and tertiary amines. The secondary and tertiary amines are by-product materials which are thought to occur by the reaction of some of the primary amine product with imine intermediate material (formed in the hydrogenation of the nitrile). In this process, the already formed primary amine reacts with imine intermediate to produce a secondary amine and, in turn, some of the secondary amine reacts with additional imine to produce a tertiary amine product.

When the starting nitrile has a multiplicity of cyano groups which are separated by an appropriate chain length of at least 2 atoms, the secondary and tertiary amine formation tends to be intramolecular to provide cyclic compounds as the dominant product. Thus, when a dinitrile, such as iminodiacetonitrile, is subjected to conventional hydrogenation, one forms the cyclic compound, piperazine, as the major material. For a trinitrile, such as nitrilotriacetonitrile, the difficulty of forming the corresponding linear aliphatic amine, tris(2-aminoethyl) amine (TREN), increases geometrically. Thus, contacting of a polynitrile with a hydrogenation catalyst is a recognized route for producing cyclic polyamines.

The use of a batch reactor has been previously viewed as a process mode which promotes the formation of unwanted side products. The batch reactor normally used in this high pressure reaction is, by conventional design, a fixed vessel in which all of the reactants are initially charged into the reaction vessel and all of the primary amine product is retained within the vessel until the process is terminated. As the nitrile is converted to imine intermediate, there is an increased probability for it to react with previously formed amine contained within the vessel and be diverted into by-product formation. Thus, when polynitriles are converted into polyamines using a conventional batch reaction, one conventionally obtains large amounts of cyclic product as well as methylated secondary amine and condensation by-products. U.S. Pat. Nos. 3,565,957 and 3,733,325 teach that the yields of cyclic amine can be optimized by carrying out the reaction in the presence of large amounts of ammonia. By using a hydrogenation catalyst to increase the yield of linear product, one produces solid condensation material which inactivates the catalyst in a very short period of time. Further, U.S. Pat. No. 3,565,957 provides an example which attempts to teach the formation of linear amine, TREN, but clearly the product formed therein is not TREN as the product has a boiling point which is distinctly different from TREN. This reference thus exemplifies the difficulty in forming desired linear polyamine product by a batch mode. The short life of the catalyst as well as low selectivity and yield has caused this process to be deemed commercially unfeasible in providing linear polyamines.

To overcome the problems associated with synthesizing aliphatic polyamines from polynitriles in batch reactors, the use of a fixed bed (trickle-bed type) reactor has been suggested by Sherwin et al. in U.S. Pat. No. 4,721,811, which is assigned to the assignee of the present invention. While the fixed bed reactor can efficiently produce large quantities of the desired amines, it cannot match the cost-effectiveness of batch-type reactor vessels when relatively smaller output is contemplated. The fixed bed process is relatively complex to set up and generally must be customized for the particular reaction to be carried out. Once set up, it is quite inefficient to modify the fixed bed reactor to accommodate a different process and then re-modify the apparatus for the original process. Thus, the fixed bed reactor process is best suited for those situations where the apparatus can be dedicated to one single reaction process. Additionally, heat removal can be a special problem with such fixed bed reactors, for example in the reduction of nitro and nitrile compounds which have very high heats of hydrogenation.

The present process would enable one to provide an efficient discontinuous or batch process carried out in a batch reactor, e.g., a stirred autoclave reactor vessel, which once the desired quantity of product is produced, is easily and cost effectively capable of being changed over to use in another process.

SUMMARY OF THE INVENTION

The present invention provides a process for the batchwise preparation of polyamines comprising hydrogenating a solution of the corresponding polynitrile in which the nitrile groups are separated by from at least 2 atoms (and thus have an atomic structure which is capable of forming a ring containing compound).

The present process requires the contacting of a polynitrile having its cyano groups separated by from at least 2 atoms, preferably 2 to 6 atoms, with a chromium containing Raney ® cobalt catalyst under hydrogen pressure. The polynitrile is introduced into the reaction vessel as a solution over substantially the entire time the process is carried out and at a rate such that the molar concentration of nitrile in the reaction zone is below 3 percent of the concentration of the feed supply throughout the reaction.

DETAILED DESCRIPTION

The present invention is directed to a fed-batch process which provides for the preparation of an aliphatic polyamine from its corresponding polynitrile. The present invention is directed to a process which uses a combination of specific parameters to unexpectedly provide a means of forming aliphatic primary amines in high conversion and selectivity from polynitriles, provides extended catalyst activity and permits production of purified material by yielding a product stream which can be readily separated.

The term "fed-batch" reactor described in the present specification and appended claims is a reactor which has a reaction zone in which at least one liquid (e.g., polynitrile solution) reactant is introduced into the reaction zone over substantially the entire time of the batch reaction. The reactants are contained therein and the products remain therein until completion of the batch reaction. A fed-batch reactor is distinct in use and design from a batch reactor (in which the reactants, the charge, are introduced into the reaction zone before the process is begun and the reactants and products are allowed to remain in the reaction zone until completion of the batch reaction, as defined by a preset time, yield or both).

The term "polynitrile" as used herein and in the appended claims defines compounds having at least two cyano groups separated by an immediate chain of at least 2 atoms, preferably 2 to 6 atoms. The cyano groups may be separated by hydrocarbon chains which are saturated or contain olefinic (ethylenic) unsaturation therein or may contain a heteroatom such as nitrogen, oxygen, sulfur, and the like or combinations thereof. Specifically, the most applicable polynitriles are nitrilotriacetonitrile, iminodiacetonitrile and ethylenediaminetetraacetonitrile as these materials provide highly desired noncyclic polyamines in an economical manner. Other polynitriles include oxidiacetonitrile, thiodiacetonitrile, 2-methylglutaronitrile and 1,3-dicyanopropene. These compounds are normally viewed as having the proper atom chain length to intramolecularly react and form stable cyclic compounds as the dominant product. However, the present process provides a means to cause the dominant product to be an aliphatic, noncyclic polyamine.

The term "polyamine" as used herein and in the appended claims refers to compounds having a plurality of amino groups corresponding to the polynitrile structure, above, wherein each nitrile is converted into a primary —CH$_2$NH$_2$ group.

The process involves contacting, preferably in a stirred or otherwise well agitated autoclave reactor vessel, a polynitrile and catalyst with hydrogen gas under pressure. The catalyst is a finely divided chromium-modified ("chromium-promoted") Raney ® cobalt. A valuable modification to the process includes conducting the hydrogenation in the presence of ammonia.

The process must be carried out in a fed-batch reactor capable of having a solution of the polynitrile reactant introduced into the reaction zone from the time of commencement of the reaction to a time substantially that of completion of the batch reaction. The solution of polynitrile should be added to the reaction zone at a space velocity such that the rate of addition of the polynitrile is not greater than the maximum rate at which the polynitrile within the reaction zone is reacting with hydrogen. It is preferred that the gradual addition of the polynitrile reactant be conducted at a space velocity such that the molar concentration of polynitrile within the reactor is equal to or less than three (3) mole percent of the polynitrile within the feed solution. This relationship of feed concentration to reaction zone concentration can be readily monitored by conventional means, such as, in which the reaction zone concentration is monitored by gas chromatography or the like and the reactant solution income flow rate is adjusted accordingly.

Typically, the gradual addition of the polynitrile reactant should be conducted at a rate such that the space velocity of the polynitrile is within the range of 0.1 to 7.0, preferably from 0.8 to 1.2, unit weight of polynitrile per unit weight of catalyst per hour. Most preferred space velocity may vary depending upon the polynitrile used. For example, it is most preferred that the polynitrile IDAN is gradually added at a rate such that the space velocity is within the range of about 1.0 to about 6.2 units weight of polynitrile per unit weight of catalyst per hour. The polynitrile NTAN, on the other hand, is most preferably added at a rate such that the space velocity is within the range of 0.8 to 1.4 unit weight of polynitrile per unit weight of catalyst per hour. Most preferred space velocities for polynitriles can be readily determined by those skilled in the art by conventional techniques.

For purpose of the invention, the term "space velocity" is used herein to indicate the unit of weight of polynitrile fed into the reactor per hour divided by the unit weight of catalyst in the fed-batch reactor. When the rate of addition of polynitrile is above the hereinstated space velocity, the desired polyamine yield and selectivity drastically diminish and the catalyst activity is shortened so that the catalyst is not suitable for subsequent runs (thus increasing the cost of the process).

The volumetric feed rate can also be calculated for any concentration of polynitrile solution and properly maintained to achieve the required feed of polynitrile to the reaction zone by insuring that a reaction parameter K, which is defined below, is maintained at a numerical value of at least 25 or greater. The parameter K for any particular system can be defined as:

$$K = \frac{163 \, WP}{nv_f} \cdot e^{-\frac{4026}{T+273}}$$

wherein
W = amount of catalyst in the reaction zone in kilograms;
P = hydrogen pressure in the reaction zone in atmospheres;
T = reaction zone temperature in °C.;
n = numbers of nitrile groups per mole of polynitrile feed; and $$v_f = \frac{(m_f^{nitrile} + m_f^{solvent})^2}{1069 \, m_f^{nitrile} + 945 \, m_f^{solvent}}$$

where
$m_f^{nitrile}$ = the mass feed rate of the polynitrile in kilograms per hour into the reactor; and $m_f^{solvent}$ = the mass feed rate of the solvent in kilograms per hour into the reactor.

The polynitrile must be introduced into the reaction zone as a liquid and, therefore, is normally introduced as a solution in a solvent medium. Solvents suitable for this purpose include amides such as N,N-dimethylacetamide (DMAC), formamide, N,N-dimethylformamide (DMF) and the like; ethers, such as dimethoxypropane, dioxane and the like as well as other solvents which are inert to the reactants and the products in the reaction zone and are capable of remaining liquid under the reaction conditions. It is preferred that the polynitrile be introduced as a solution at concentrations of from 5 wt. percent to saturation, preferably from 5 to 30 wt. percent based on the total weight of the liquid solution introduced into the reaction zone. Higher concentrations can be utilized, e.g., up to about 70 wt. percent, when the feed solution is maintained at an elevated temperature. Because the polynitriles are soluble in the commonly employed solvents, a substantially saturated solution of polynitrile is consequently preferred. For example, in the preferred DMAC solvent, it is possible to obtain a fully saturated solution of about 22.5% by weight NTAN at ambient conditions. The employment of a "substantially saturated" solution of about 20% by weight of NTAN in DMAC, or about 25% by weight in DMF, is preferred to avoid the possibility of having the polynitrile come out of solution during the processing. After preparation, the solution is sparged with nitrogen until all air is removed. The feedstock solution is maintained under a nitrogen blanket pending further use.

It is understood that the specific polynitrile reactant chosen will determine the primary polyamine product to be formed. Each cyano group will be converted to a primary methyleneamine group. It has been found that when using the present process, the hydrogenation selectivity goes to the formation of primary amine product without any major interaction between the formed methyleneamine and the intermediate imine groups and especially substantially low intramolecular reaction and without the formation of N-methylated product.

The catalyst required to perform the present process is a finely-divided chromium containing Raney® cobalt which has a particle size of from 20 to 50 microns mean diameter. The Raney® cobalt catalyst should contain from about 0.5 to about 10, preferably about 2 to 5, wt.% of chromium. About 2.5 weight percent of chromium is most preferred. The catalyst may also contain up to about 5 weight percent nickel and preferably contains about 1 to 4 percent nickel.

The catalyst is relatively sensitive to oxygen and thus must be handled carefully to avoid surface oxidation. The catalyst particles are washed with deionized and deaerated water and then with a deaerated inert solvent (preferably the same solvent used to prepare the feedstock solution) prior to use. The catalyst should be charged into the reactor in an amount of from about 5% to 30%, preferably 10% to 15% and most preferably about 15% by weight based on the weight of the polynitrile to be reacted in a particular run.

The catalyst is formed from an initial alloy which contains from about 50 to 70 wt. percent aluminum, from about 30 to 50 wt. percent cobalt and varying amounts of chromium and, optionally, nickel. Chromium may also be provided by treating the surface of an already activated alloy with a salt of these materials to provide from 0.1 to about 5 percent of chromium on the Raney® cobalt surface. The catalyst is formed from alloys having from about 0 to 6, preferably 0.5 to 5.0, wt.% of chromium.

The catalyst can be prepared by contacting the initial alloy with an aqueous alkaline solution formed from an alkali or alkaline earth metal hydroxide, preferably sodium hydroxide. The alloy should have a particle size of from about 20 to 50 microns mean diameter. The activation is carried out in known manners by contacting the starting alloy with dilute, normally from about 1 to 10 wt. percent, preferably from 1 to 5 wt. percent, of an alkaline solution while maintaining a low temperature such as below about 50° C. and preferably below 40° C. Generally, it is best to activate the alloy at from about 20° to 40° C. Activation is readily monitored by the evolution of hydrogen and provides a suitable catalyst for use in the present process when from 20 to 40 percent of the aluminum is removed. The activated Raney cobalt catalyst is washed with water to free it from the alkaline solution and used immediately or stored under water or other inert medium or atmosphere.

As mentioned above, the chromium promoted Raney® cobalt hydrogenation catalyst is quite sensitive to oxygen and thus oxygen should be excluded from each of the reactants and from the reaction vessels to the greatest extent possible. Nitrogen sparging of the reactant solutions and the storage of the same under nitrogen blankets is effective to exclude oxygen from the system.

Suitable hydrogenation reactor apparatuses preferred for carrying out the inventive process are known per se. A preferred type of fed-batch apparatus, the stirred autoclave, consists of a pressure vessel fitted with an agitator with cooling coils for heat removal and a means for introducing the feedstock solution during the pressurized reaction. Either an internal heating coil or an external heating jacket are employed to initially raise the reactants to a sufficient temperature. Also suitable is the so-called pump-loop reactor (e.g., manufactured by Buss, Pratteln, Switzerland).

Following completion of the hydrogenation reaction, the liquid contents of the vessel are separated from the solid catalyst. This separation can be accomplished by discharging the entire contents of the reactor vessel into a holding tank and then filtering the catalyst, or by allowing the catalyst to settle in the reactor and then removing the supernatant liquid via a dip tube in the reactor vessel. The catalyst has been found to retain its activity even after utility of numerous batch reactions when performed according to the present process. Therefore, utilization of fresh catalyst for each batch is not required when practicing the present process.

The particulars of the present inventive process includes:

Polynitrile feed solution: The polynitrile feedstock solution should be formed with a solvent which is inert to the reaction conditions found in the reaction zone and to the polynitrile reactant and polyamine product. Such solvents are discussed above. The concentration of polynitrile in the feedstock solution should be determined to maintain the proper rate of introduction of feedstock during the course of the batch reaction.

The Catalyst: The catalyst, as described above, should be added to the reaction zone under a nitrogen or other inert gas blanket. The catalyst is added in excess, preferably the catalyst is added in an amount of from about 5 to 30%, most preferably about 15%, by weight based on the weight of the polynitrile to be consumed during the fed-batch operation.

Ammonia: The presence of ammonia has been seen to improve the ratio of linear polyamine to the cyclic by-product in the overall reaction product. The molar ratio of ammonia to nitrile group of a given polynitrile reactant may range from 0 to above 10 with from about 1 to 7 and especially about 5 to 6 being preferred.

Temperature: The reactor is heated to a temperature sufficient to start the hydrogenation reaction, for example to a temperature ranging from about 90° to 150° C., preferably from about 100° C. to 130° C.

Pressure: The hydrogen pressure within the reaction zone should be maintained at a pressure in excess of 750 psig, preferably from about 1000 to 3000 psigs, most preferably from 1500 to 3000 psig. The overall pressure maintained in the reaction zone should be sufficient to maintain the polynitrile, and the solvent in a liquid state. The hydrogen pressure described above may be supplemented by partial pressure formed from an inert gas, such as nitrogen.

Polynitrile Feed: As stated above, the polynitrile should be introduced into the fed-batch reactor over the major time period of the batch reaction. The rate of introduction is to be governed by the molar concentration of the polynitrile in the feed solution and in the reaction zone as fully disclosed hereinabove. It has been unexpectedly found that by carrying out the batch process in a fed-batch manner, as described herein, one minimizes formation of cyclic by-product, minimizes the formation of condensation products, minimizes the formation of N-methylated amines of the corresponding desired product, produces a reaction product from which the desired polyamine is readily separated, and minimizes the deactivation of the catalyst and thus permits its reuse in subsequent runs.

The process can be conducted by sparging the reaction zone with an inert gas such as nitrogen and charging the zone with a heel of deaerated inert solvent of sufficient volume to make contact with the agitator and the temperature sensor. The catalyst is then charged to the reaction zone under a blanket of nitrogen. At this point, anhydrous ammonia may also be added. The reaction zone is then heated and charged with hydrogen pressure and the introduction of polynitrile solution into the reaction zone is commenced. The hydrogen pressure is generally maintained at a fixed level by continuous addition.

An extended fed-batch reaction can also be practiced. In this case, once the reactor has been filled to its maximum operating level, continuation of the polynitrile feed can be maintained by the simultaneous withdrawal of filtered reaction product (free of catalyst) so as not to exceed the maximum operating level.

The following examples are given for illustrative purposes only and are not meant to be a limitation on the present invention as defined by the claims appended hereto. All parts and percentages are by weight unless otherwise stated.

EXAMPLE 1

Into a one liter stainless steel autoclave previously flushed with nitrogen is charged 250 milliliters of dimethyl acetamide solvent along with 5.9 grams of solvent washed chromium promoted Raney® cobalt. Anhydrous ammonia (53.0 grams, 3.12 moles) was also added to the autoclave which was then heated to 90° C. and pressurized to 1000 psig with hydrogen. This temperature and pressure was maintained throughout the run.

A deaerated solution of iminodiacetonitrile (IDAN) in dimethylacetamide (125 grams, 23.7 wt.% IDAN) at room temperature was fed to the autoclave by a metering pump at a space velocity of 1.0 grams of IDAN per grams of catalyst per hour. The rate of addition was 0.43 ml/minute over a period of 306 minutes. At the completion of the reaction the contents of the autoclave were removed and the catalyst filtered. Analysis of the filtrate showed the yield of diethylene triamine (DETA) to be 43.3% of theoretical. The reaction parameter K, for this reaction was 19.9, lower than the desired range, which accounts for the low yield. The amount of N methylated diethylene triamine impurity present amounted to 7.0% of the DETA product.

EXAMPLES 2-6

The procedure of Example 1 was repeated except that conditions were varied to operate over a range of temperatures, pressures, space velocities and K values. The conditions and results are shown in Table 1 attached.

TABLE 1

| Example | Temperature °C. | Temperature °K. | Pressure psig | Pressure atm | Catalyst grams | DMAC Heel Charge nds | Ammonia Charge grams | IDAN Feed Conc'n wt. % | Run Time hrs |
|---|---|---|---|---|---|---|---|---|---|
| 1 | 90 | 363 | 1000 | 69 | 5.9 | 250 | 53 | 23.7 | 5.1 |
| 2 | 90 | 363 | 1000 | 69 | 11.8 | 250 | 56 | 23.7 | 5.3 |
| 3 | 90 | 363 | 1000 | 69 | 12.5 | 250 | 31 | 23.7 | 2.9 |
| 4 | 125 | 398 | 1500 | 103 | 5.9 | 250 | 26 | 23.7 | 5.1 |
| 5 | 125 | 398 | 1500 | 103 | 5.9 | 250 | 26 | 23.7 | 3.3 |
| 6 | 125 | 398 | 1500 | 103 | 27.9 | 150 | 125 | 23.7 | 2.9 |

| Example | IDAN Feed Rate g/hr | IDAN Feed Sol'n grams | Space Velocity | K | DETA Yield mole % | N-Methyl DETA/ DETA % |
|---|---|---|---|---|---|---|
| | 5.88 | 125 | 1.0 | 19.9 | 43.3 | 7.0 |
| | 11.35 | 250 | 1.2 | 20.6 | 15.9 | N.A. |
| | 11.35 | 139 | 0.94 | 21.8 | 34.8 | N.A. |
| | 5.88 | 125 | 1.0 | 52.6 | 82.7 | 1.7 |
| | 5.88 | 125 | 1.0 | 52.6 | 82.0 | N.A. |
| | 41.0 | 494 | 6.2 | 35.7 | 79.0 | 1.6 |

N.A. = Not Available

EXAMPLE 7

Chromium-promoted Raney® cobalt (12.5 g) was washed with deaerated dimethyl formamide (DMF) and added to a one liter autoclave, previously flushed with nitrogen, containing 250 ml deaerated DMF. Anhydrous ammonia (34.0 g, 2 moles) was also added and the autoclave then was heated to 100° C. and pressurized to 1500 psig with hydrogen. This temperature and pressure was maintained throughout the run.

A deaerated solution of nitrilotriacetonitrile (NTAN) in DMF (195 ml, 25 wt. % NTAN) was fed to the autoclave by a metering pump at a space velocity of 0.4. The rate of addition of NTAN was approximately the same rate at which it was reacted (approx. 1 ml/min.) over the course of 560 minutes. At the completion of the reaction, the contents of the autoclave were removed and the catalyst filtered. Analysis of the filtrate (592.0 g) showed the yield of TREN to be 79.6% of the theoretical value. The reaction parameter K was 60.9 for this run.

EXAMPLE 8

Following the procedure of Example 7, chromium promoted Raney® cobalt (4.9 g), anhydrous ammonia (34.0 g) and 250 ml deaerated DMF were added to the oxygen-free autoclave which was then heated to 120° C. and pressurized to 1500 psig with hydrogen. A deaerated solution of NTAN in DMF (195 ml, 25 wt.% NTAN) was fed to the autoclave at a space velocity of 1.02. Analysis of the filtrate (495.3 g) from the reaction mixture showed a yield of 76.2% TREN. The reaction parameter K is 45.6 for this run.

EXAMPLE 9

The run described in Example 7 was repeated except that the 195 ml of 5 wt. % NTAN in DMF was all added at the beginning of the run prior to pressurization to 3000 psig with hydrogen and heated up to 100° C. The yield of TREN dropped to 9% and the catalyst was found to have lost more than half its activity when it was reused.

A second run was conducted similar to that described in Example 7 except 150 gm deaerated DMAC was initially charged followed by 111 gm anhyd. ammonia and 500 gm DMAC solution having 25% IDAN (124 gm). All were added at the beginning of the run. The reactor was then pressurized and heated to 1500 psig $H_2$ and 125° C. for 5 hours. The yield of DETA was 0.5%.

These runs show that when a typical batch process is carried out, very low yield and selectivity is obtained and the catalyst is poisoned.

EXAMPLES 10-15

The procedure of Example 7 was repeated except that dimethylacetamide was used as the solvent and conditions were varied to operate over various ranges of space velocities. The conditions and results are shown in Table II attached.

TABLE 2

Effect of Space Velocity on TREN Yield

| Example | Temperature °C. | Temperature °K. | Pressure psig | Pressure atm | Catalyst grams | DMAC Heel Charge nds | Ammonia Charge grams | NTAN Feed Conc'n wt. % | Run Time hrs | NTAN Feed Rate g/hr | Space Velocity | K | TREN Yield % |
|---|---|---|---|---|---|---|---|---|---|---|---|---|---|
| 10 | 120 | 393 | 1500 | 102 | 7.3 | 250 | 34 | 20.3 | 7.0 | 6.9 | 0.95 | 41.2 | 74.7 |
| 11 | 120 | 393 | 1500 | 102 | 4.9 | 250 | 34 | 20.5 | 9.5 | 5.1 | 1.05 | 37.1 | 74.3 |
| 12 | 120 | 393 | 1500 | 102 | 4.0 | 250 | 34 | 19.6 | 6 | 4.8 | 1.20 | 30.8 | 69.7 |
| 13 | 120 | 393 | 1500 | 102 | 4.0 | 250 | 34 | 19.7 | 6 | 5.4 | 1.35 | 27.9 | 76.2 |
| 14 | 120 | 393 | 1500 | 102 | 4.0 | 250 | 34 | 19.3 | 6 | 6.0 | 1.50 | 23.1 | 40.8 |
| 15 | 120 | 393 | 1500 | 102 | 4.0 | 250 | 34 | 18.7 | 6 | 3.1 | 0.80 | 47.4 | 74.8 |

EXAMPLE 16

Following the procedure of Example 7, chromium promoted Raney® cobalt (4.2 g) and 250 ml of deaerated dimethylacetamide (DMAC) were added to the oxygen-free autoclave. A deaerated solution of nitrilotripropionitrile (NTPN) in DMAC (260 ml, 5.0 wt. % NTPN) was fed to the autoclave by a metering pump at a space velocity of 1.0 gram per gram of catalyst. The yield of tris(3-aminopropyl) amine was in excess of 90%.

While it is apparent that preferred embodiments of the invention are herein disclosed, it is appreciated that the invention is susceptible to modifications, variations and changes without departing from the scope or fair meaning of the appended claims.

WHAT IS CLAIMED:

1. A process for the batchwise hydrogenation of polynitrile to noncyclic, aliphatic polyamine compound comprising:
a) providing a feedstock solution of an aliphatic polynitrile;
b) providing a fed-batch reactor vessel containing a finely-divided chromium containing Raney® cobalt catalyst in a substantially oxygen-free atmosphere;
c) introducing the polynitrile into the reactor vessel gradually over substantially the entire time of the hydrogenation reaction at a space velocity such that the rate of addition of the polynitrile is no greater than the maximum rate at which the polynitrile reacts with the hydrogen wherein the volumetric feed rate of the polynitrile is such that it provides a reaction parameter K, having a value of about 25 or greater, which is defined by the equation:

$$K = \frac{163\ WP}{nvf} \cdot e^{-\frac{4026}{T+273}}$$

wherein
W = amount of catalyst in the reaction zone in kilograms;
P = hydrogen pressure in the reaction zone in atmospheres;
n = the number of nitrile groups per mole of feed;
T = reaction zone temperature in ° C.; and $$v_f = \frac{(m_f^{nitrile} + m_f^{solvent})^2}{1069 \, m_f^{nitrile} + 945 \, m_f^{solvent}}$$

where $m_f^{nitrile}$ = the mass feed rate of the polynitrile in kilograms per hour into the reactor; and $m_f^{solvent}$ = the mass feed rate of the solvent in kilograms per hour into the reactor;

d) hydrogenating the polynitrile by contacting said polynitrile with hydrogen in the reactor vessel at a temperature and pressure sufficient to initiate the hydrogenation to produce as the dominant product a noncyclic, aliphatic compound having a plurality of amino groups which corresponds to the nitrile groups of the starting polynitrile; and e) recovering said noncyclic, aliphatic polyamine compound.

2. The process of claim 1 wherein the polynitrile is introduced into the reactor vessel at a space velocity of from about 0.1 to about 6.2 grams of polynitrile per gram of catalyst per hour and is hydrogenated at a temperature of 90° C. to 125° C. and a pressure in excess of 1000 psig.

3. The process of claim 1 or 2 wherein the polynitrile is nitrilotriacetonitrile and the polyamine product is tris(2-aminoethyl) amine.

4. The process of claim 1 or 2 wherein the polynitrile is iminodiacetonitrile and the polyamine product is diethylenetriamine.

5. The process of claim 1 or 2 wherein the polynitrile is ethylenediaminetetraacetonitrile and the polyamine product is tetrakis(2-aminoethyl) ethylenediamine.

6. A process of claims 1, 2, 3, 4 or 5 further comprising adding anhydrous ammonia to the reactor vessel in an amount of about 1 to about 10 moles of ammonia per mole of nitrile group contained in the polynitrile.

7. A process of claims 1, 2, 3, 4, or 5 wherein the catalyst is chromium-containing Raney ® cobalt containing from 0.5 to 10 wt.% chromium and having a particle size of about 20 to about 50 microns mean diameter.

8. A process of claims 1, 2, 3, 4 or 5 wherein said feedstock solution comprises a substantially saturated solution of polynitrile in inert solvent.

9. A process of claims 1, 2, 3, 4 or 5 wherein said catalyst is present in an amount of from about 5 to about 30 percent by weight based on the weight of the polynitrile to be consumed during the fed-batch reaction.

10. The process of claims 1, 2, 3, 4 or 5 wherein the polynitrile is introduced into the reactor vessel at a rate such that the molar concentration of polynitrile within the reactor is equal to or less than three (3) mole percent of the polynitrile within the feed solution.

11. The process of claim 2 wherein the polynitrile is introduced into the reactor vessel at a rate such that the molar concentration of polynitrile within the reactor is equal or less than three (3) mole percent of the polynitrile within the feed solution.

12. The process of claim 3 wherein the polynitrile is introduced into the reactor vessel at a space velocity of from about 0.8 to about 1.4 grams of polynitrile per gram of catalyst per hour and is hydrogenated at a temperature of about 100° C. to 130° C. and a pressure of about 1500 to 3000 psig.

13. The process of claim 4 wherein the polynitrile is introduced into the reactor vessel at a space velocity of from about 1.0 to about 6.2 grams of polynitrile per gram of catalyst per hour and is hydrogenated at a temperature of about 100° C. to 130° C. and a pressure of about 1500 to 3000 psig.

14. The process of claim 1 or 2 wherein the process is conducted by an extended fed-batch reaction.

* * * * *